United States Patent [19]
Fischell et al.

[11] Patent Number: 5,697,971
[45] Date of Patent: Dec. 16, 1997

[54] MULTI-CELL STENT WITH CELLS HAVING DIFFERING CHARACTERISTICS

[76] Inventors: Robert E. Fischell, 14600 Viburnum Dr., Dayton, Md. 21036; David R. Fischell, 71 Riverlawn Dr., Fair Haven, N.J. 07704; Tim A. Fischell, 1018 Chancery Dr., Nashville, Tenn. 37215

[21] Appl. No.: 661,562

[22] Filed: Jun. 11, 1996

[51] Int. Cl.$^6$ .................................... A61F 2/06
[52] U.S. Cl. .................... 623/1; 623/11; 623/12; 606/192; 606/195
[58] Field of Search .................... 623/1, 11, 12

[56] References Cited

U.S. PATENT DOCUMENTS

| | | | |
|---|---|---|---|
| 4,739,762 | 4/1988 | Palmaz | 128/343 |
| 5,102,417 | 4/1992 | Palmaz | 606/195 |
| 5,197,978 | 3/1993 | Hess | 623/1 |
| 5,383,892 | 1/1995 | Cardon et al. | 606/198 |
| 5,395,390 | 3/1995 | Simon et al. | 606/198 |
| 5,449,373 | 9/1995 | Dinchasik et al. | 606/198 |

FOREIGN PATENT DOCUMENTS

0540290A2   5/1993   European Pat. Off. .

OTHER PUBLICATIONS

"New Beginnings–Great Endings"–1995 Johnson and Johnson Int. Systems advertisement.

*Primary Examiner*—John G. Weiss
*Assistant Examiner*—John M. Black

[57] ABSTRACT

The present invention is a multi-cell stent having at least two different types of cells with each type of cell accomplishing a different purpose. For example, a first type of cell is intended to provide a maximum radial rigidity after stent deployment. A second type of cell is designed to provide increased longitudinal flexibility prior to stent deployment and after stent deployment into a main artery, the second type of cell can be readily balloon expanded at the ostium of a side branch artery to a comparatively large diameter without breaking any of the struts of the stent cell. By this technique, unobstructed blood flow into the side branch can be provided.

20 Claims, 4 Drawing Sheets

MULTI-CELL STENT WITH CELLS HAVING DIFFERING CHARACTERISTICS

FIELD OF USE

The present invention is an expandable stent insertable into a vessel of a human body for the purpose of creating and maintaining the patency of that vessel.

BACKGROUND OF THE INVENTION

Some of the earliest stents were merely helical coils that expanded radially outward after being placed in a vessel of a human body. More recent stents have used uniform cellular structures with the stent typically being expanded radially outward into a vessel by means of a balloon located at a distal portion of a balloon angioplasty catheter. After radial expansion, some of these stents have struts or wires that tend to block a side branch artery which comes off a main artery into which the stent has been placed. With an expandable balloon, it is possible to break open a strut of a particular cell of such a stent where the struts of that cell are impeding blood flow into that side branch. However, breaking open such a cell can leave strut ends protruding into the lumen of the side branch or the main artery itself which is highly undesirable. Also, breaking a cell open weakens the stent structure.

SUMMARY OF THE INVENTION

The present invention is a multi-cell stent having at least two different types of cells with each type of cell accomplishing a different purpose. For example, a first type of cell is intended to provide a maximum radial rigidity after stent deployment. A second type of cell is designed to provide increased longitudinal flexibility prior, to stent deployment and after stent deployment into a main artery, the second type of cell can be readily balloon expanded at the ostium of a side branch artery to a comparatively large diameter without breaking any of the struts of the stent cell. By this technique, unobstructed blood flow into the side branch can be provided.

Thus an object of this invention is to have a multi-cell stent with at least two different types of cells.

Another object of this invention is to have a stent in which one type of cell has enhanced radial rigidity after stent deployment and a second type of cell provides increased flexibility prior to deployment and after deployment that cell can be balloon expanded into a generally circular shape thereby causing all stent struts to be moved away from the opening of a side branch of a main artery.

Still another objective of this invention is to have ring-like, cylindrical segments of the stent which segments are made up of only one type of cell of the multi-cell stent.

These and other important objects and advantages of this invention will become apparent from the detailed description of the invention and the associated drawings provided herein.

DETAILED DESCRIPTION OF THE INVENTION

Figure 1:
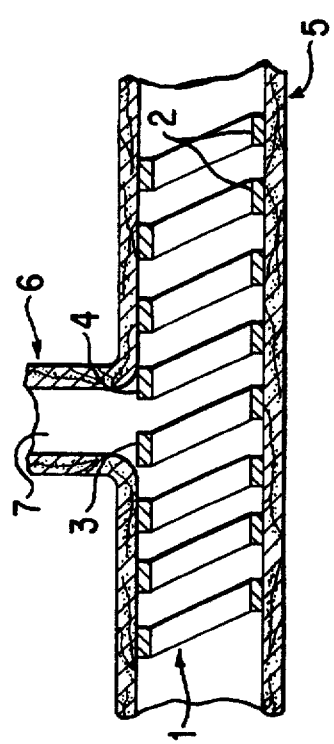
FIG. 1 is a cross-sectional view of a main artery with a prior art stent deployed with partial blockage of the side branch.

FIG. 1 shows a prior art stent 1 that has been deployed radially outward into a main artery 5. The stent 1 has many struts (or wires) 2, and specifically, strut segments 3 and 4 of two such wires 2 have been deployed in such a manner as to partially obstruct the ostium or mouth of the side branch artery 6. This condition has been termed "stent jail". Because of the obstructing position of the segments 3 and 4, blood flow into the lumen 7 of the side branch 6 is compromised. Furthermore, the wires 3 and 4 can block the passage of a second stent from entering the lumen 7 of the side branch 6.

Figure 2:
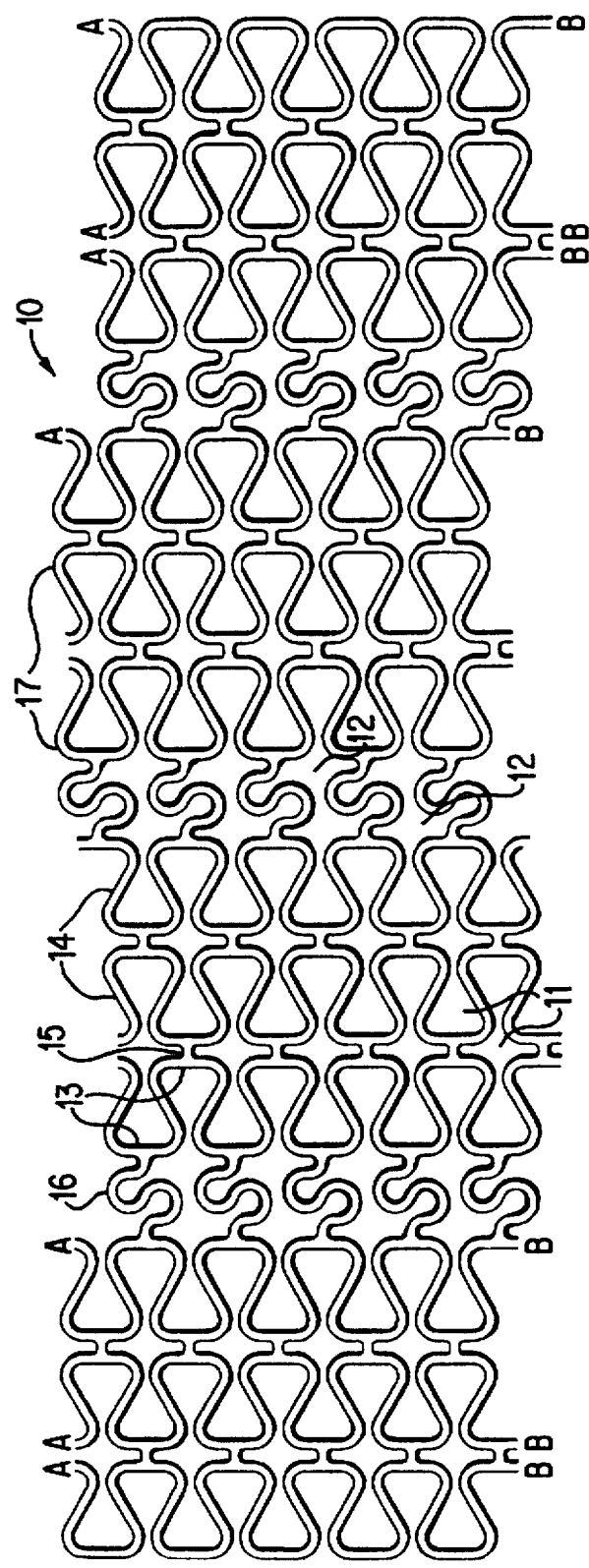
FIG. 2 illustrates one embodiment of the present invention represented as a flat, 2-dimensional plan view of a multi-cell cylindrical stent prior to deployment.

One embodiment of the present invention as shown in FIG. 2, is a pre-deployed cylindrical stent 10 as it would appear if it were cut longitudinally and then extended out into a flat, 2-dimensional configuration. It should be clearly understood that the stent 10 is in fact cylindrical in shape, which cylindrical shape would be obtained by rolling the flat configuration of FIG. 2 into a cylinder with all points "A" joined to all points "B". The stent 10 is typically fabricated by laser machining of a thin-walled, cylindrical, stainless steel tube.

The stent 10 has exactly two different types of cells: namely, structural cells 11 and special expandable cells 12. Both these cells are formed from vertical struts 13 each having two curved end sections 17, each end section being joined to a diagonal strut 14. Some of the vertical struts 13 are joined with horizontal H-bars 15 which form part of the perimeter of the cells 11, and some of the vertical struts 13 are joined by undulating S-struts 16 which form part of the perimeter of the expandable cells 12.

Figure 3:
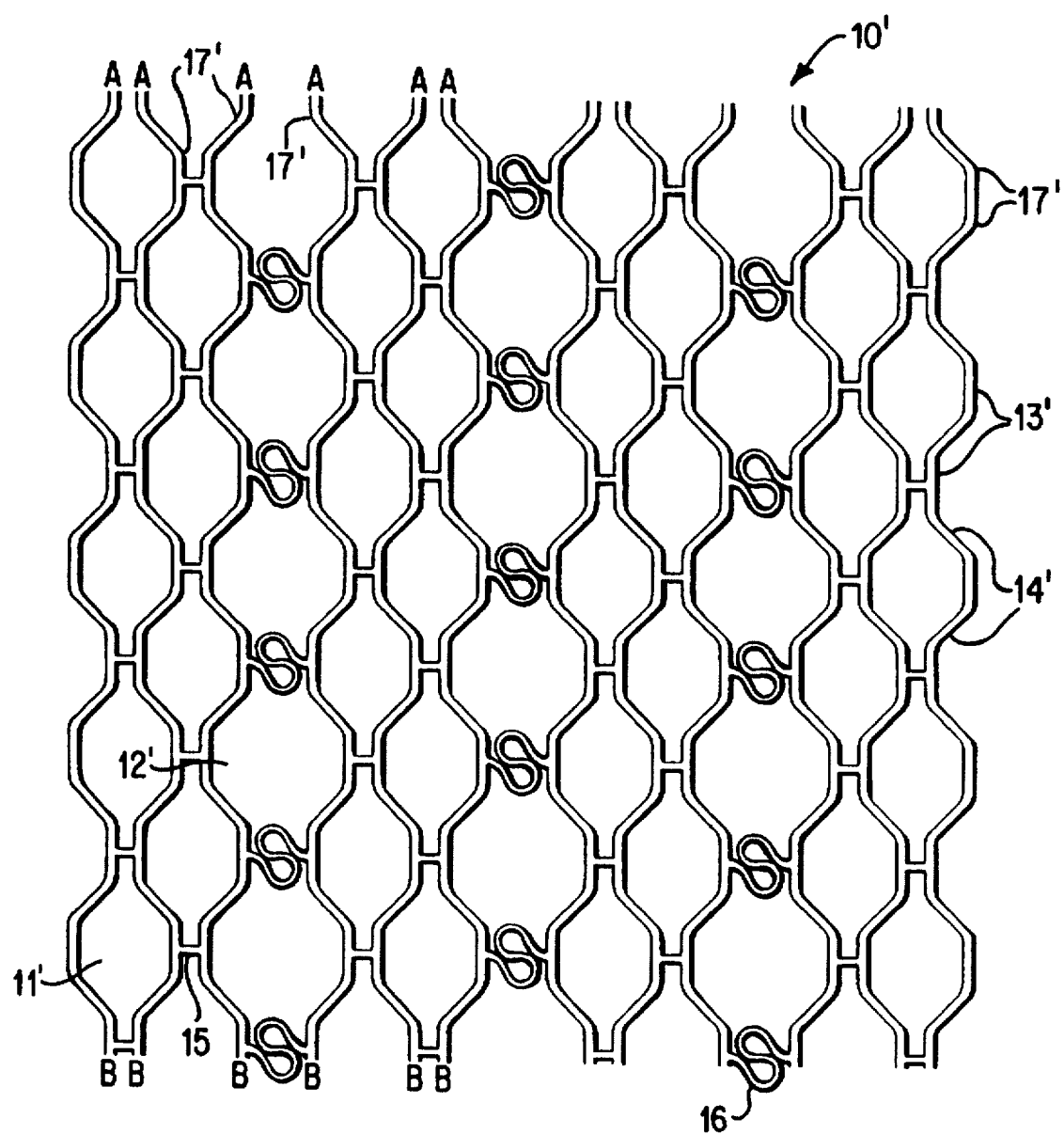
FIG. 3 shows a 2-dimensional representation of the cylindrical stent of FIG. 2 as it would appear after deployment.

FIG. 3 is a 2-dimensional representation of the cylindrical stent 10' after deployment; i.e., after radially outward dilatation. FIG. 3 shows how the pre-deployed stent 10 of FIG. 2 is configured after deployment to the stent 10' shown in FIG. 3. FIG. 3 also shows the deployed structural cells 11', the deployed special expandable cells 12', the vertical struts 13', the diagonal struts 14', the curved end sections 17' the H-bars 15 and the S-struts 16. Neither the H-bars 15 nor the S-struts 16 change shape when the stent 10 is deployed to form the stent 10'.

It should be noted that both the cells 11 and 11' and 12 and 12' are formed into ring-like circumferential, cylindrical segments with (in this case) exactly five cells per cylindrical segment. Typically, a multi-cell stent would have at least three cells per cylindrical segment disposed circumferentially, and all cylindrical segments are one cell wide in the longitudinal direction. From either FIG. 2 or FIG. 3 it is clear to see that the stent 10 or 10' has exactly 8 cylindrical segments of structural cells 11 and 3 cylindrical segments of expandable cells 12 or 12'.

Prior to deployment, the S-struts of the stent 10 provide greatly enhanced longitudinal flexibility for the stent 10. This allows for easier placement of the stent 10 through highly curved coronary arteries. FIGS. 2 and 3 clearly show that the H-bar 15 is much shorter in length as compared to the S-strut 16. Therefore, the perimeter of the cells 12' is significantly longer that the perimeter of the cells 11'. Therefore as compared to a cell 11', not only is it easier to expand a cell 12' by placing a balloon within that cell and inflating that balloon to a high pressure, but any cell 12' is also expandable to a greater diameter as compared to any cell 11'. Ideally, the perimeter length of the expandable cell 12' should be at least 10 percent longer that the perimeter length of the cells 11'.

Figure 4A:
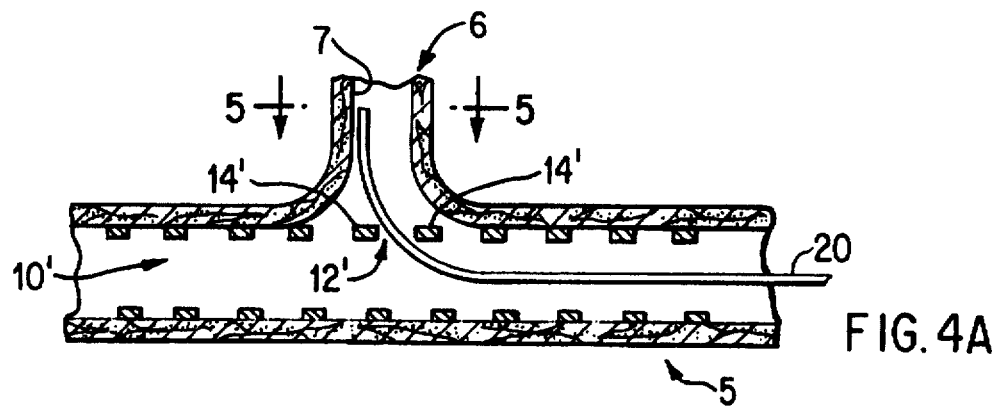
FIG. 4A illustrates a deployed multi-cell stent placed in a main artery with some stent struts partially blocking a side branch artery.
Figure 4B:
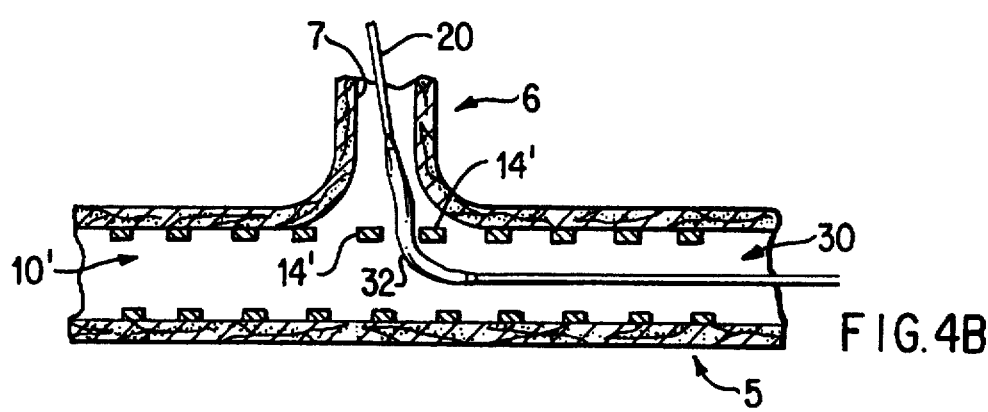
FIG. 4B illustrates the deployed stent of FIG. 4A with an inflatable balloon advanced over a guide wire and into the side branch artery.
Figure 4C:
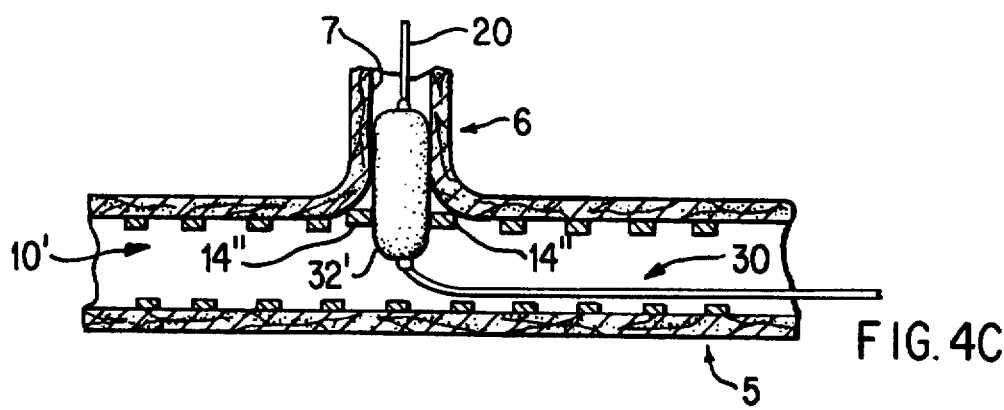
FIG. 4C shows the balloon of FIG. 4B expanded so that the stent struts are pushed away from the ostium of the side branch artery.
Figure 4D:
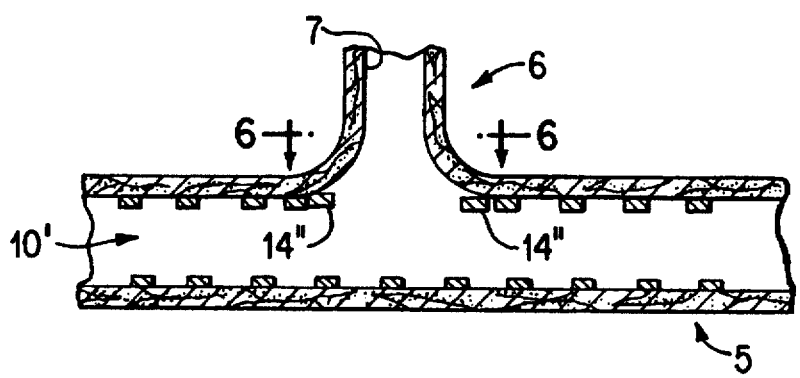
FIG. 4D shows the guide wire and balloon removed with the stent struts no longer blocking the ostium of the side branch artery.

FIG. 4A shows the stent 10' deployed into a main artery 5 with two of the diagonal struts 14' blocking the lumen 7 of the side branch 6. It should be noted that the struts 14' would be part of the perimeter of an expanded cell 12'. A guide wire 20 can be placed through the expandable cell 12', and the guide wire 20 can then be advanced into the lumen 7 of the side branch 6. As shown in FIG. 4B, a balloon angioplasty catheter 30 can then be advanced over the guide wire 20, through the expanded cell 12', and into the lumen 7. As seen in FIG. 4B, the balloon 32 is placed mostly into the side branch 6, but it also extends partially into the main artery 5. A liquid at a pressure of at least 3 atmospheres, (but typically 10 to 16 atmospheres), is then injected into the balloon 32 which causes it to become the inflated balloon 32' as shown in FIG. 4C. The inflated balloon 32 causes longitudinal displacement of the diagonal struts 14' so as to form the struts 14" which become part of the newly shaped stent 10" both as shown in FIG. 4C. Furthermore, the inflated balloon 32' causes the perimeter of the expandable cell 12' to assume a generally circular shape without the breakage of any strut. The balloon 32' is then deflated, and the guide wire 20 and balloon angioplasty catheter 30 are removed from the side branch artery 6 and the main artery 5. The stent 10" then appears as shown in FIG. 4D. It should be pointed out that the balloon 32' can not only move struts so as to "unjail" a side branch, but the balloon 32' can also perform balloon dilatation of any stenotic narrowing at or near the ostium (or mouth) of any side branch artery into which the balloon 32' is advanced.

For the sake of clarity, FIGS. 4A, 4B, 4C and 4D show only those parts of the stent 10' and 10" that are located at the center of the main artery 5.

Figure 5:
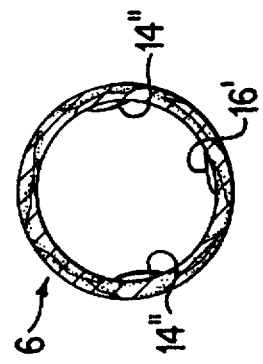
FIG. 5 is an enlarged cross-sectional view looking down the side branch artery at section 5—5 of FIG. 4A.

FIG. 5 is a cross-sectional view looking down the side branch artery 6 showing the portion of the stent 10' that has been deployed into the ostium of the side branch artery 5. Note that the S-strut 16 has not changed in shape when the stent 10 is deployed into the main artery to form the stent 10'. Although the cell 12' is more open that the cell 12, the diagonal struts 14', the vertical struts 13' and the S-strut 16 each can cause some blockage of the ostium of the side branch artery 6.

Figure 6:
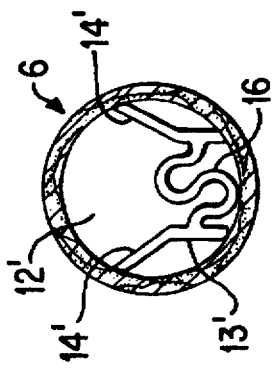
FIG. 6 is an enlarged cross-sectional view looking down the side branch artery at section 6—6 of FIG. 4D.

FIG. 6 is a cross-sectional view looking down the side branch artery 6 after the balloon 32 has been inflated to form the balloon 32' and the balloon angioplasty catheter 30 has been removed. Only that portion of the stent 10" which is positioned at the ostium of the side branch 6 is shown in FIG. 6. It is easily seen that virtually all of the struts that were shown in FIG. 5 to be blocking blood flow to the side branch artery 6 have been moved aside. Specifically, the diagonal struts 14' have been moved away from the center of the ostium of the side branch to form the struts 14", and the S-strut 16 has been moved aside to form the S-strut 16'. Therefore, blood flow to the side branch artery 6 is improved, and one could then readily place another stent (not shown) through the ostium and into the lumen 7 of the side branch artery 6 in order to treat an ostial stenosis (not shown).

Figure 7:
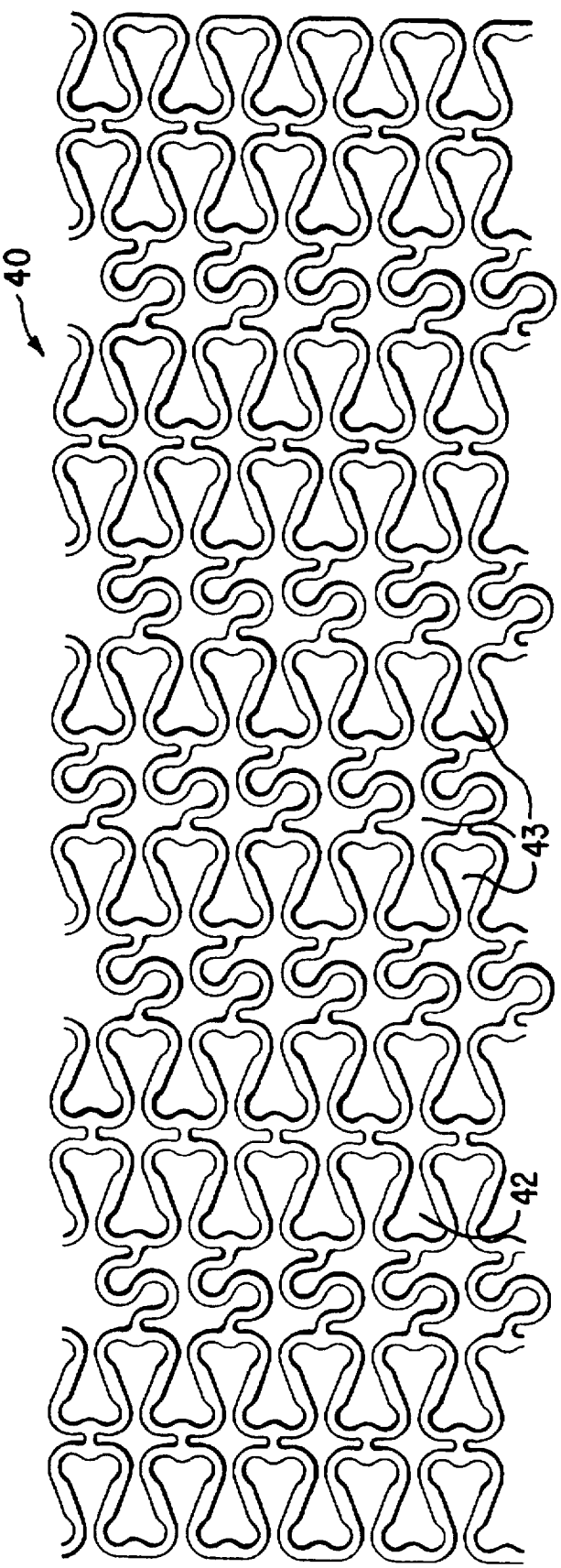
FIG. 7 is a 2-dimensional representation of an alternative embodiment of the present invention in which a multi-cell, pre-deployed stent has three cylindrical segments of special expandable cells placed at the center of the stent.

FIG. 7 shows a 2-dimensional view of a pre-deployed stent 40 which is a second embodiment of the present invention. Like the stent 10, the stent 40 is ideally suited for placement at the ostium of a side branch artery. The stent 40 has three circumferential cylindrical segments of the special expandable cells 43 placed at the longitudinal center of the stent 40. All other cells of the stent 40 are structural cells 42. Having three cylindrical segments of special expandable cells 13 at the center of the stent 40 has the advantage of requiring less accuracy for the placement of the center of the stent 40 at a side branch artery.

The fact that both the stents 10 and 40 have cylindrical segments in which all the cells of one segment are identical makes it possible for the stent implanting physician to place a special expandable cell at a side branch without requiring any knowledge of the stent's angular position about the stent's longitudinal axis. This would not be the case if there was more than one type of cell in a cylindrical segment.

Although the description herein has been applied only to the vessels that are arteries, it should be understood that the apparatus and method described herein could also be applied to other types of vessels of the human body such as bronchial tubes in the lung or the bile duct in the liver.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A multi-cell stent structure integrally formed as a thin-walled cylinder, the stent having a multiplicity of cells each having a closed perimeter formed from thin, wire-like struts and curved sections and each cell having two longitudinally separated ends, the perimeter of at least some of the cells of the multi-cell stent including a pair of vertical struts extending in a generally circumferential direction and being longitudinally displaced each with respect to the other at the longitudinally separated ends of each cell, each vertical strut having two curved end sections each being joined to a diagonal strut thereby forming a pair of diagonal struts connected to the two curved end sections of each vertical strut, at least one cell of the multi-cell stent being an expandable cell which includes within the perimeter at least one undulating strut, the undulating strut being adapted to provide increased longitudinal flexibility to the multi-cell stent and each expandable cell having a longer perimeter length as compared to the perimeter length of at least one other type of cell of the multi-cell stent.

2. The stent of claim 1 wherein there are not more than two different types of cells which make up the multi-cell stent.

3. The stent of claim 1 wherein the undulating strut of the expandable cell is an S-strut which provides the stent with additional longitudinal flexibility prior to stent deployment, the S-strut also providing additional perimeter length for each expandable cell as compared to the perimeter length of the at least one other cell of the multi-cell stent.

4. The stent of claim 1 wherein the expandable cells have a perimeter length that is at least 10% greater as compared to the perimeter length of the at least one other type of cell.

5. The stent of claim 1 wherein the at least one other type of cell is adapted for increasing post-deployment radial rigidity and the expandable cell is adapted to be expanded to a generally circular shape by means of an inflatable balloon that is placed through the closed perimeter of the expanded cell, the balloon being inflated within the expandable cell to a pressure exceeding three atmospheres.

6. The stent of claim 1 wherein the stent consists of a multiplicity of cylindrical segments, each cylindrical segment consisting of only one type of cell, each cylindrical segment having at least three cells disposed circumferentially and being one cell wide in the longitudinal direction.

7. The stent of claim 6 wherein the stent has at least one cylindrical segment of expandable cells which expandable cells are adapted to be expanded to a generally circular shape by means of an inflatable balloon that is placed through the closed perimeter of an expandable cell and then inflated within that cell to a pressure exceeding three atmospheres.

8. The stent of claim 6 wherein the stent has at least three cylindrical segments of expandable cells.

9. The stent of claim 8 wherein the stent has a longitudinally centered, center section into which three adjacent cylindrical segments of expandable cells are located.

10. The stent of claim 5 wherein the stent has a longitudinal axis and the inflatable balloon has a longitudinal axis and the inflatable balloon is placed through one expandable cell with its longitudinal axis placed approximately perpendicular to the longitudinal axis of the stent.

11. A multi-cell stent adapted for placement at a side branch artery of a main artery of the human body, the stent structure being in the general form of a thin-walled cylinder consisting of a multiplicity of cells, each cell having a closed perimeter consisting of a series of wire-like struts and curved sections which are integrally joined together, the stent having a first type of cell, said cell having a perimeter including at least one undulating strut adapted to increase the stent's flexibility, the perimeter of the first type of cell being greater in length as compared with the perimeter length of a second type of cell of the stent, the stent also having a longitudinally centered, center section wherein at least one cylindrical segment is located, each cylindrical segment at the stent's center section consisting of at least three of the first type of cells placed circumferentially and being one cell wide in the longitudinal direction.

12. The stent of claim 11 wherein there are not more than two different types of cells which make up the multi-cell stent.

13. The stent of claim 11 wherein the undulating strut of the first type of cell is an S-strut which provides the stent with additional longitudinal flexibility prior to stent deployment, the S-strut also providing additional perimeter length for the first type of cell as compared to the perimeter length of the second type of cell.

14. The stent of claim 11 wherein the first type of cell has a perimeter length that is at least 10% greater as compared to the perimeter length of the second type of cell.

15. The stent of claim 11 wherein the second type of cell is adapted for increasing post-deployment radial rigidity and the first type of cell is adapted to be expanded to a generally circular shape by means of an inflatable balloon that is placed through the closed perimeter of the first type of cell, the balloon being inflated within that first type of cell to a pressure exceeding three atmospheres.

16. The stent of claim 11 wherein the stent consists of a multiplicity of cylindrical segments, each cylindrical segment consisting of only one type of cell, each cylindrical segment having at least three cells disposed circumferentially and being one cell wide in the longitudinal direction.

17. The stent of claim 16 wherein the stent has at least one cylindrical segment of the first type of cells which cells are adapted to be expanded to a generally circular shape by means of an inflatable balloon that is placed through the closed perimeter of the first type of cell and then inflated within that cell to a pressure exceeding three atmospheres.

18. The stent of claim 16 wherein the stent has at least three cylindrical segments consisting of only the first type of cells.

19. The stent of claim 18 wherein the stent has a longitudinally centered, center section into which three adjacent cylindrical segments of the first type of cells are located.

20. The stent of claim 17 wherein the stent has a longitudinal axis and the inflatable balloon has a longitudinal axis and the inflatable balloon is placed through one of the first type of cells with its longitudinal axis placed approximately perpendicular to the longitudinal axis of the stent.

* * * * *